United States Patent [19]
Jorgensen et al.

[11] Patent Number: 6,073,500
[45] Date of Patent: Jun. 13, 2000

[54] ULTRA-ACCELERATED NATURAL SUNLIGHT EXPOSURE TESTING

[75] Inventors: Gary J. Jorgensen, Pine; Carl Bingham, Lakewood; Rita Goggin, Englewood; Allan A. Lewandowski, Evergreen; Judy C. Netter, Westminster, all of Colo.

[73] Assignee: Midwest Research Institute, Kansas City, Mo.

[21] Appl. No.: 09/006,746

[22] Filed: Jan. 13, 1998

[51] Int. Cl.⁷ ................................................. G01N 17/00
[52] U.S. Cl. ..................... 73/865.6; 126/573; 126/685; 359/853; 374/57
[58] Field of Search .............................. 73/865.6; 374/57; 359/853; 126/573, 685, 692

[56] References Cited

U.S. PATENT DOCUMENTS

| | | | |
|---|---|---|---|
| 1,827,530 | 10/1931 | Le Grand | 73/865.6 X |
| 2,945,417 | 7/1960 | Coryl et al. | 73/150 R X |
| 3,501,942 | 3/1970 | Fitzgerald et al. | 374/57 |
| 3,686,940 | 8/1972 | Kockott | 73/159 X |
| 4,012,954 | 3/1977 | Klippert | 73/150 R |
| 4,391,522 | 7/1983 | Schmid et al. | 73/150 R X |
| 4,627,287 | 12/1986 | Suga | 73/865.6 |
| 4,760,748 | 8/1988 | Katoyonogi et al. | 73/865.6 |
| 4,799,390 | 1/1989 | Kimura | 73/865.6 |
| 4,807,247 | 2/1989 | Robbins, III | 374/57 |
| 4,817,447 | 4/1989 | Kashima et al. | 73/865.6 |
| 4,995,273 | 2/1991 | Kisimo et al. | 75/865.6 |
| 5,138,892 | 8/1992 | Suga | 73/865.6 |
| 5,153,780 | 10/1992 | Jorgensen et al. | 359/853 |
| 5,305,634 | 4/1994 | Suga et al. | 73/865.64 |
| 5,568,366 | 10/1996 | Jefferies | 73/865.6 |
| 5,618,863 | 4/1997 | D'Errico et al. | 524/91 |
| 5,646,358 | 7/1997 | Tikhtman et al. | 73/865.6 |
| 5,854,433 | 12/1998 | Patel et al. | 73/865.6 |

FOREIGN PATENT DOCUMENTS

| | | | |
|---|---|---|---|
| 19632349 | 1/1998 | Germany | |
| 32847 | 2/1984 | Japan | 374/57 |
| 61648 | 3/1989 | Japan | 73/865.6 |

*Primary Examiner*—Thomas P. Noland
*Attorney, Agent, or Firm*—Ken Richardson

[57] ABSTRACT

Process and apparatus for providing ultra accelerated natural sunlight exposure testing of samples under controlled weathering without introducing unrealistic failure mechanisms in exposed materials and without breaking reciprocity relationships between flux exposure levels and cumulative dose that includes multiple concurrent levels of temperature and relative humidity at high levels of natural sunlight comprising:
  a) concentrating solar flux uniformly;
  b) directing the controlled uniform sunlight onto sample materials in a chamber enclosing multiple concurrent levels of temperature and relative humidity to allow the sample materials to be subjected to accelerated irradiance exposure factors for a sufficient period of time in days to provide a corresponding time of about at least a years worth of representative weathering of the sample materials.

12 Claims, 13 Drawing Sheets

ULTRA-ACCELERATED NATURAL SUNLIGHT EXPOSURE TESTING

CONTRACTUAL ORIGIN OF THE INVENTION

The United States Government has rights in this invention pursuant to Contract No. DE-AC36-83CH10093 between the United States Department of Energy and the Midwest Research Institute.

BACKGROUND

1. Field of the Invention

This invention relates to a process for subjecting materials to accelerated irradiance exposure factors that permit about a year's worth of representative weathering to be accumulated in a period from about 3 to about 10 days, under controlled weathering conditions that include several concurrent levels of temperature and relative humidity at very high levels of natural sunlight.

In the invention process, a solar concentrator [which may include a High Flux Solar Furnace (HFSF) and an Irradiance Redistribution Guide (IRG)] is used to obtain elevated levels(25–100×) of concentrated sunlight for accelerated testing of material samples.

When an IRG is used, it provides the unique capability of being able to modify (redistribute) the Gaussian-shaped beam from the HFSF into a more uniform profile on a sample exposure plane.

By adequately controlling sample temperatures and demonstrating that reciprocity relationships are obeyed (i.e., level of applied accelerated stresses does not change failure/degradation mode), this novel capability allows materials to be subjected to accelerated irradiance exposure factors of 25–100×, thereby permitting a year's worth of representative weathering (in terms of natural sunlight exposure) to be accumulated in from about 3 to about 10 days.

2. Description of the Prior Art

U.S. Pat. No. 4,817,447 discloses a weathering chamber using lamps and sample temperature control using cooling air. Uniform sample irradiance at accelerated levels of up to 10 suns (within the UV bandwidth) appear attainable.

A test apparatus incorporating a mirror which rejects infrared is disclosed in U.S. Pat. No. 4,012,954. In the '954 patent, convective cooling air and a conductive substrate are also incorporated. However, although convective cooling is used, the air movement is not used to deliver humidity to the samples during exposure; rather, humidity is provided by floating the sample substrate in a water bath. Further, as in the case of U.S. Pat. No. 4,817,447, the '954 patent uses artificial light sources for exposure of the samples.

U.S. Pat. No. 3,686,940 discloses a water-cooled cylindrical mirror which rejects infrared radiation in an ultraviolet test apparatus. In the '940 patent, natural sunlight is not used.

A solar weathering device with control of sample temperature by cooling air is disclosed in U.S. Pat. No. 4,807,247. While this patent uses natural sunlight, a sample irradiance at accelerated levels of up to only 8 suns across the complete solar spectrum is employed.

U.S. Pat. No. 5,138,892 discloses accelerated light fastness testing of materials with xenon lamps and sample temperature control using air flow. Sample irradiance at accelerated UV levels of up to 8 suns (180 W/m² between 300–400 nm) are attainable. This patent does not utilize natural sunlight in its testing of materials.

A weather test machine using xenon lamps and sample temperature and humidity control using air flow is disclosed in U.S. Pat. No. 5,646,358. Uniform sample irradiance at accelerated levels up to only 1–3 suns (within the UV bandwidth) are attainable. This patent does not utilize natural sunlight in its weather test machine.

U.S. Pat. No. 5,153,780 discloses a dish reflector and method for concentrating moderate solar flux uniformly on a target plane, said dish having stepped reflective surface characterized by a plurality of ring-line segments arranged about a common axis, each segment having a concave spherical configuration.

3. The Need for Capabilities Beyond the Prior Art

There is a need for devising facilities for ultra-accelerated natural sunlight exposure testing of materials and devices under controlled weathering conditions that include several concurrent levels of temperature and relative humidity at very high levels of natural sunlight. This need is associated with the desirability to be able to predict the in-service lifetimes of said materials and devices from correlations derived between such realistically accelerated test results and those obtained during normal use conditions. Further, there is a need to conduct these ultra-accelerated exposure tests at irradiance exposure factors of from about 25 to 100 suns, wherein the irradiance is highly uniform. Lastly, the need to conduct these ultra-accelerated natural sunlight exposure tests of materials and devices should exclude artificial light sources which invariably introduce uncertainties regarding realistic spectral content of the irradiance stress on samples being exposed. For example, the use of artificial light leads to unrealistic degradation mechanisms and failure modes of exposed materials caused by low wavelength (<300 nm) photons that are not present in terrestrial solar spectra.

SUMMARY OF THE INVENTION

In light of the drawbacks of the foregoing prior art, a general object of the invention is to provide the unique capability to carry out ultra accelerated exposure testing of materials and devices under controlled conditions that include several concurrent levels of temperature and relative humidity at very high levels of natural sunlight, thereby permitting about a year's worth of representative weathering, in terms of natural sunlight exposure, to be accumulated in from about 3 to about 10 days.

Another object of the present invention is to provide or make use of a solar concentrator (which may include an HFSF and an IRG) to provide an elevated level of sunlight having a uniform profile on a sample exposure plane. When the HFS and IRG is used the unique capability to redistribute the highly concentrated Gaussian-shaped beam from the HFSF to a more uniform profile on the sample exposure plane is also provided.

A further object of the present invention is to provide ultra accelerated exposure testing of materials and devices by controlling sample temperatures and humidities and demonstrating that reciprocity relationships are obeyed (i.e., level of applied accelerated stress does not change failure/degradation mode).

A yet further object of the present invention is to provide ultra-accelerated exposure testing of materials and devices that allows materials to be subjected to accelerated irradiance exposure factors of 25–100× to provide about a year's worth of representative weathering, in terms of natural sunlight exposure, to be accumulated in from about 3 to about 10 days.

A still further object of the invention is to provide a method of carrying out ultra accelerated exposure testing of materials and devices utilized a sample chamber that allows control of temperature and humidity during light exposure; wherein concentrated sunlight enters the chamber through an appropriate window, which may include quartz.

A further object yet still of the invention is to provide a method for carrying out ultra accelerated exposure testing of materials and devices utilizing a cold mirror as a filter that reflects the ultraviolet/visible (UV/VIS) and transmits the near infrared (NIR) part of the solar spectrum, since the short wavelength (UV) light has been shown to be the predominant deleterious stress experienced by materials and devices during outdoor weathering.

Another object of the present invention is to provide a method of carrying out ultra accelerated exposure testing of materials and devices under controlled weathering conditions, wherein conductive cooling of sample materials is provided by a water cooled substrate on to which samples are placed, and convective cooling is provided by blowing moist or dry air over the top surface of the samples, to provide high or low humidity to the samples during exposure of redirected concentrated sunlight into the exposure chamber to reduce the thermal load on the samples.

In general, the invention is accomplished by the steps of: utilizing a solar concentrator to obtain elevated levels (25–100×) of concentrated sun light on the materials or samples being tested; converting the Gaussian-shaped beam from the solar concentrator (for example, a HFSF) into a uniform flux profile having a given diameter (preferably as extended as 10 cm diameter) in the sample exposure plane (using, for example, a unique IRG; utilizing a cold mirror to reflect deleterious ultraviolet/visible (UV/VIS) light into the sample chamber; transmitting concentrated near-infrared (NIR) radiation to minimize undesirable thermal loading of material samples; and further control of temperature and relative humidity experienced by materials samples within the exposure chamber.

BRIEF DESCRIPTION OF THE DRAWINGS

The drawings which are incorporated in and form part of the specification will illustrate preferred embodiments of the invention, and serve together with the description to explain the principles of the invention wherein:

FIG. 3 shows the sample exposure chamber detail design that allows two levels of temperature and two levels of relative humidity to be maintained during sunlight exposure for the apparatus of the invention and ability to monitor spatial and spectral uniformity of the solar beam in situ during sample exposure.

DETAILED DESCRIPTION OF THE INVENTION

Figure 1A:
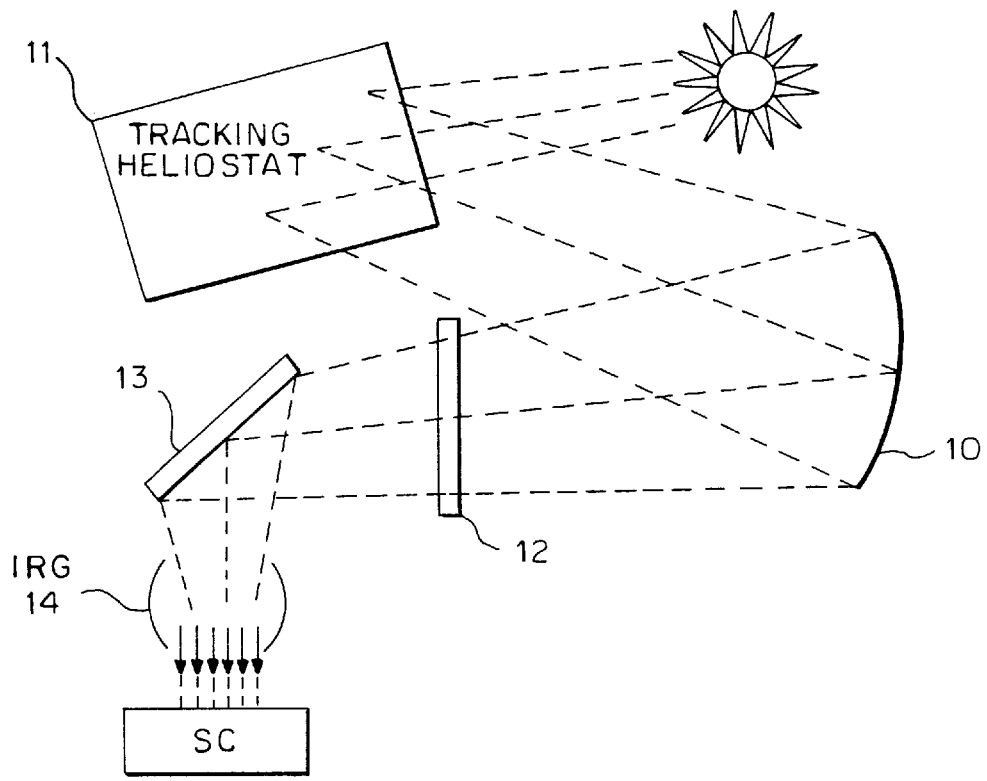
FIG. 1a depicts apparatus showing a vertically disposed irradiance redistribution guide that provides the capability of redistributing a solar beam from the HFSF without the use of a cold mirror but requiring a hot mirror as the sample exposure chamber window.

As can be seen from FIG. 1a, sunlight is continually directed onto a primary concentrator array 10 of the HFSF by a tracking heliostat 11. Concentrated sunlight passes through an attenuator 12 to a turning mirror 13 and then to a secondary concentrator (IRG) 14. The exposure port (window) on the top of the chamber was designed to be a "hot mirror" to allow ultraviolet (UV) and visible (VIS) sunlight to be incident on the samples being tested in sample chamber SC, but to reflect the near infrared (NIR) part of the solar spectrum to minimize the thermal load on the samples. The chamber intended to be used in this initial design only allowed sample exposure at a single control temperature and relative humidity.

Figure 1B:
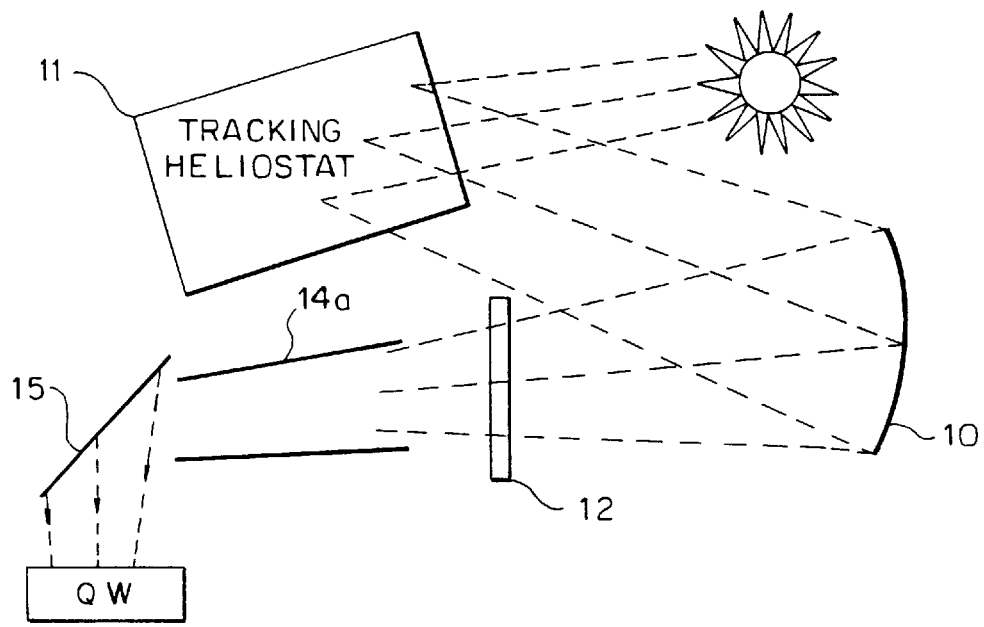
FIG. 1b depicts the invention apparatus showing a substantially horizontally disposed irradiance redistribution guide that provides the capability of redistributing the Gaussian-shaped beam from the HFSF utilizing a cold mirror to provide a spectrally selective uniform profile on a sample exposure plane.

It was discovered that all state-of-the-art NIR reflective coatings would also absorb sunlight below about 375 nm, thereby blocking much of the degradation-causing radiation from the exposed samples (290–375 nm photons present in the terrestrial solar spectrum). Consequently, the system design was modified as shown in FIG. 1b to position the IRG (14a) horizontally, thereby eliminating the need for a turning mirror, and incorporating or using a cold mirror 15 at ≈45° between the IRG and the sample chamber (so as to keep the sample chamber horizontal) and replace the sample chamber cold mirror window with a highly transmissive quartz plate. The cold mirror was found to reflect ultraviolet and visible light (UV/VIS) down through the highly transmissive quartz window QW, and allow the concentrated NIR to be transmitted (i.e., not directed onto the samples).

The IRG provides the unique capacity of being able to modify (redistribute) the Gaussian-shaped beam from the primary concentrator to a more uniform profile on a plane located a sufficient distance behind the IRG.

The IRG was designed to provide a uniform concentration of up to 400×(400 kW/m$^2$ flux at nominal solar irradiance levels) within a 10 cm diameter spot at the optimal sample plane (this means that a new IRG may also be adjusted to provide a uniform concentration of 100× over a 20 cm diameter spot, ultimately allowing a four-fold increase in the number of samples that could be exposed at this nominal intensity). For normal materials (e.g., other than concentrator PV modules designed to take advantage of such elevated flux), lower concentration levels are needed to provide accelerated exposure conditions without destroying the samples. The spatial uniformity of the incident flux was measured using a fiber-probe spectral beam characterization system. This new measurement system was also sed to monitor, in situ, optical performance of sample materials being weathered.

Figure 2:
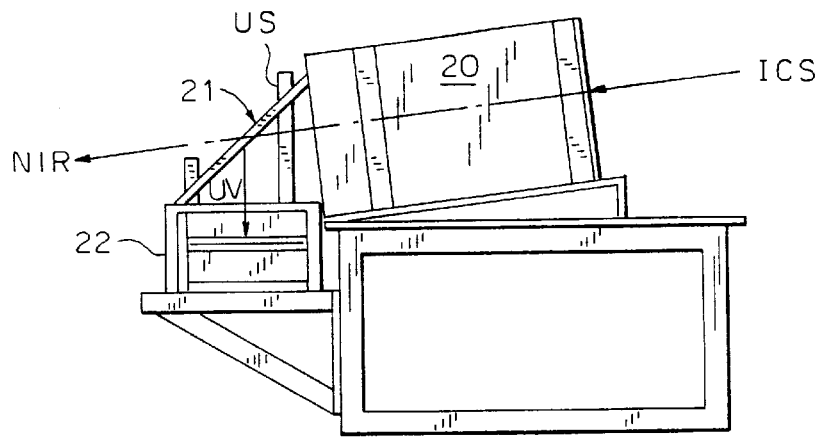
FIG. 2 is a perspective view of the system layout of the apparatus of the invention showing the sample chamber interface, via a cold mirror, with the HFSF/IRG components.
Figure 3A:
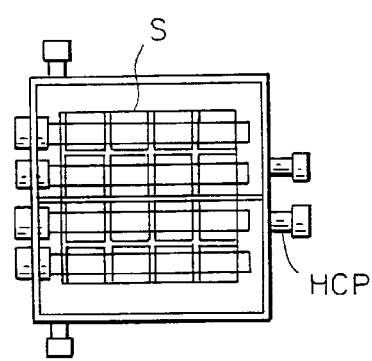
FIG. 3a shows a top view of the heating/cooling chamber with samples in place.
Figure 3B:
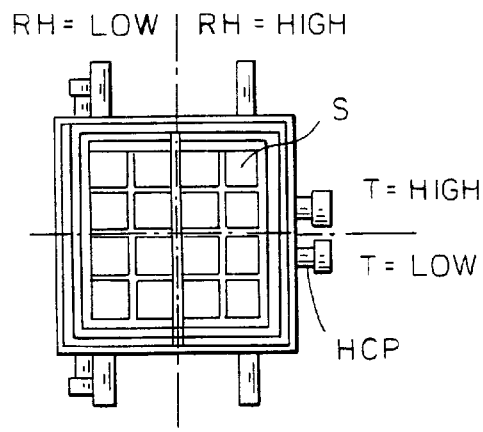
FIG. 3b shows a top view of the chamber with humidity chamber in place.
Figure 3C:
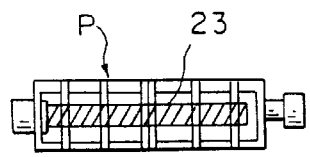
FIG. 3c is a side view of the heating/cooling chamber.
Figure 3D:
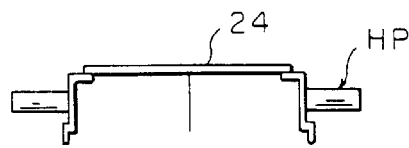
FIG. 3d is a side view of the humidity chamber.

FIG. 2 shows the cross-sectional system layout of the IRG 20, cold mirror 21 and sample chamber 22, wherein incident concentrated sunlight ICS is passed through the IRG and uniform sunlight US exits. An improved chamber was designed and fabricated that allows up to four replicate samples of about 2.2 cm×2.2 cm square in size each to be exposed to the same high level of accelerated solar flux at two levels each of temperature and humidity. For example, at a given flux (e.g., 50× suns), sets of samples can be simultaneously exposed at Tlow, RHlow, Tlow, Rhhigh; Thigh, RHlow; and Thigh, RH high. This allows a four-fold increase in experimental throughput at a particular exposure flux.

A detailed drawing of the sample exposure chamber is shown in FIG. 3. FIG. 3a is a top view of the heating/cooling chamber with samples S in place, and showing heating/cooling parts HCP. FIG. 3b is a top view of the chamber with the humidity chamber in place. During testing the samples are mechanically attached to the top surface of the heating/cooling chamberr to provide good thermal contact. The humidity chamber sits atop the heating/cooling chamber. FIG. 3c is a side view of the heating/cooling chamber, showing the pathway P for fiber optic probes and the cross section view of the heaters 23. FIG. 3d is a side view of the humidity chamber showing the humidity ports HP and the highly transmissive quartz window 24.

Demonstration of Practicality by Use of the Invention

A series of experiments were performed using three different samples (solar reflector materials), three levels of concentrated sunlight, and two controlled levels each of high and low temperature and relative humidity.

Three commercial materials (available from the 3M Company) were used in these tests. Each used approximately 1000° Å silver as the reflective layer and a pressure sensitive acrylic-based adhesive to allow lamination to 6061 aluminum substrates. The base resin of the biaxially oriented superstrate material was a polymethylmethacrylate (PMMA) film. The three materials differed primarily in the amount of UV absorber present in the PMMA film and in the type of back protective layer, as shown in the table below:

TABLE 1

Metalized polymer mirror materials used in 50X, 75X, 100X experiments

| Material | Weight % UV Absorber | Protective Back Layer |
| --- | --- | --- |
| ECP-300A | 1 | None |
| ECP-305 | 2 | None |
| ECP-305+ | 2 | 300Å Cu |

Three experiments were performed. Each was intended to expose sample materials to the equivalent of one year's outdoor exposure in Colorado, at successively higher concentrations of accelerated natural sunlight.

The first experiment used 50 suns concentration; at this level (50 kW/m$^2$, corrected for optical reflectance losses of the HFSF system), one years equivalent Colorado exposure would be obtained after 40.2 hours. Similarly, one years equivalent exposure would be accumulated after 26.8 hours at 75 suns after 20.1 hours at 100 suns.

The samples were placed in either of four areas of the chamber: hot and dry, hot and wet, cold and dry or cold and wet. The average conditions for each of the exposures is shown below.

TABLE 2

Average Exposure Conditions

| | Temperature | | Relative Humidity | |
| --- | --- | --- | --- | --- |
| Acceleration Factor (suns) | Avg Hot (° C.) | Avg Cold (° C.) | Avg Wet (% RH) | Avg Dry (% RH) |
| 50 | 63–71 | 18–23 | 55–75 | 5–10 |
| 75 | 60–75 | 17–24 | 55–70 | 5–10 |
| 100 | 65–75 | 15–25 | 60–75 | 5–10 |

During these experiments the targeted nominal temperatures were 70° C. in the hot side and the 20° C. on the cold side. The targeted relative humidity on the dry side was ≦10% and ≈80% on the wet side. The intended high relative humidity could not be maintained during on-sun experiments; roughly 70% was the best that could be achieved.

From Table 2, it can be seen that the hot temperature was maintained within the desired level. The cold temperature was usually within 5° C. of the set temperature. The dry humidity was maintained by a constant purge of dry house air, and the humid portion of the chamber was kept within 10% of the nominal targeted level.

Figure 4:
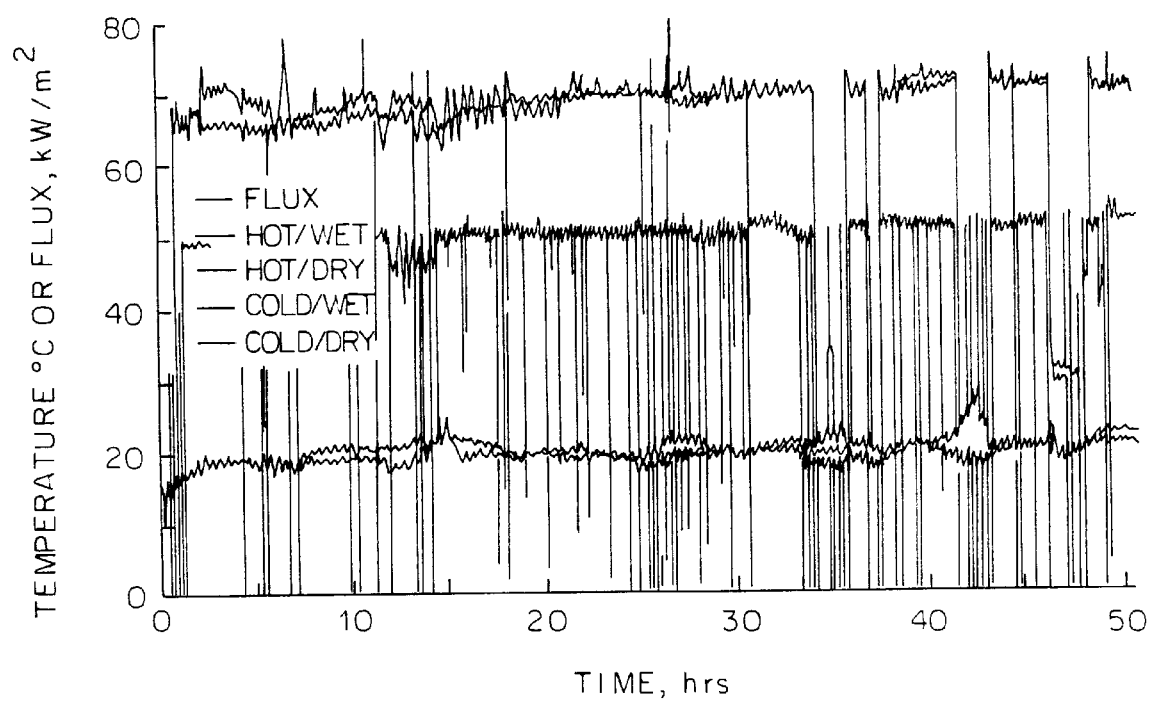
FIG. 4 is a graph showing sample temperature, humidity, and flux for 50× sun tests demonstrating the ability to maintain/control constant levels of irradiance and various combinations of temperature and relative humidity during sample exposure.

FIG. 4 presents a closer look at representative, real-time stress conditions. One minute average temperatures and flux during the 50 sun test are shown. The hot temperatures stay between 65 and 70° C. most of the time, and the cold temperatures are near 20° C. The humidity (not shown) does not seem to affect the temperatures significantly. The flux can be seen changing between 0 and 50 kW/m$^2$.

Demonstration of Best/Preferred Method

Figure 5A:
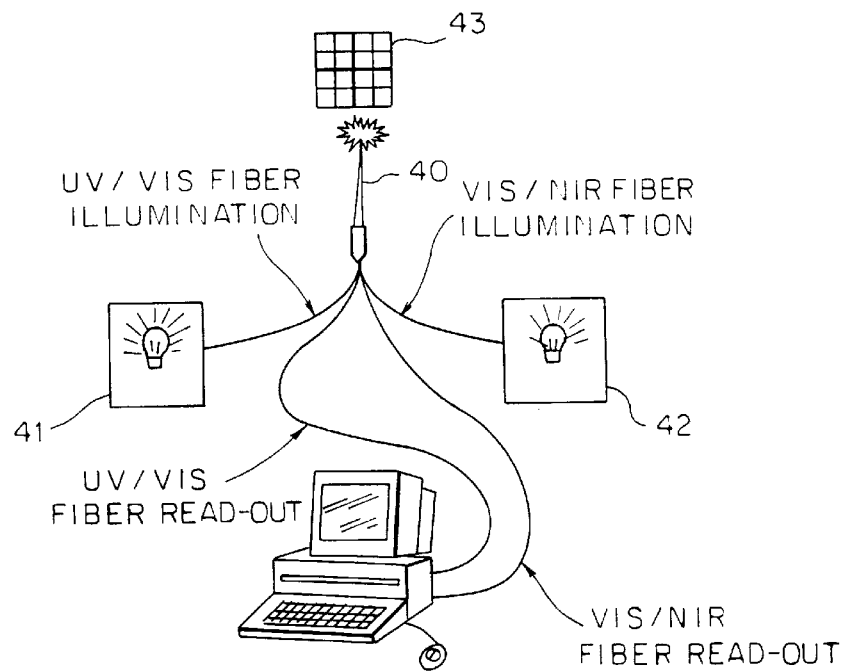
FIG. 5a is a spectroscope system operation schematic that shows how spectral reflectance measurements can be made in-situ during experiments carried out using this invention.

Spectral hemispherical reflectance, $\rho_{2\pi}(\lambda)$ of each sample was measured before exposure and after the experiment was completed using a Perkin Elmer Lambda-9 UV-VIS-NIR spectrometer. Reflectance of samples were also periodically measured in situ using a commerically available fiber optic reflectance probe system (The SpectraScope System operation schematics are shown in FIG. 5). Use of this device is shown schematically in the reflectance mode in FIG. 5a.

Figure 5B:
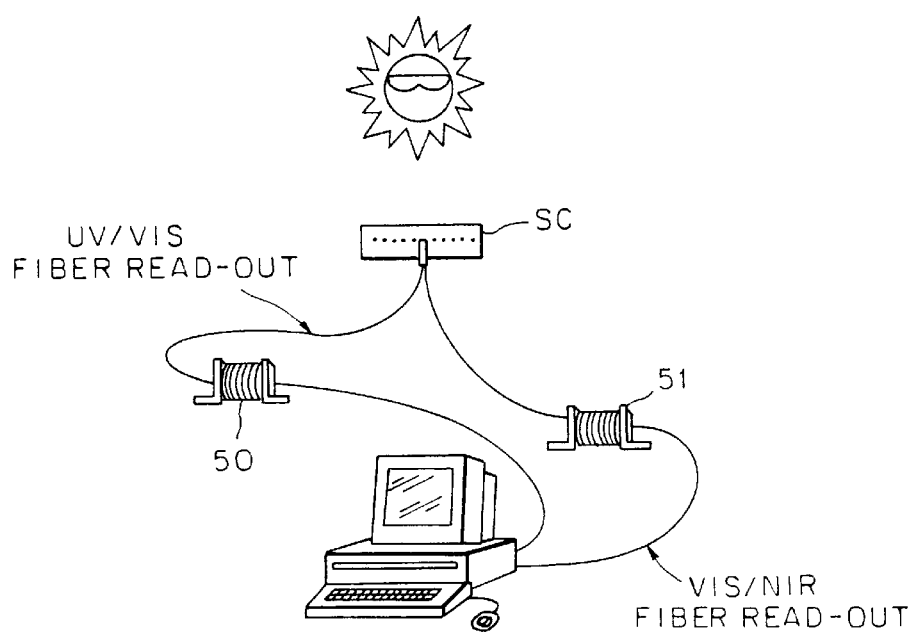
FIG. 5b is a spectroscope system operation schematic that shows how the spectral and spatial irradiance can be measured in-situ during experiments carried out using this invention.

The SpectraScope System was also used for in situ monitoring of the spectral irradiance incident upon the samples during exposure testing. In this case, the system was configured as shown in FIG. 5b. Here, ~6–7.5 cm long, stripped fibers (one each UV/VIS and VIS/NIR) were inserted up through access ports at the bottom of the sample chamber SC until their highly-polished tips were coplanar with the mirror samples being exposed to concentrated sunlight. During normal operation, spectral irradiance data was acquired at five minute (averaged) intervals at a position at the center of the samples. Additional access ports allowed spatial uniformity of the concentrated sunlight to be characterized as well.

Results

Spectral hemispherical reflectance, $\rho_{2\pi}(\lambda)$, of all samples were measured before ($\beta$) and after ($\alpha$) exposure. The amount of degradation experienced during exposure was then computed as the difference (loss) in reflectance: $\Delta\rho = \rho_{2\pi,\beta}(\lambda) - \rho_{2\pi,\alpha}(\lambda)$.

Figure 6A:
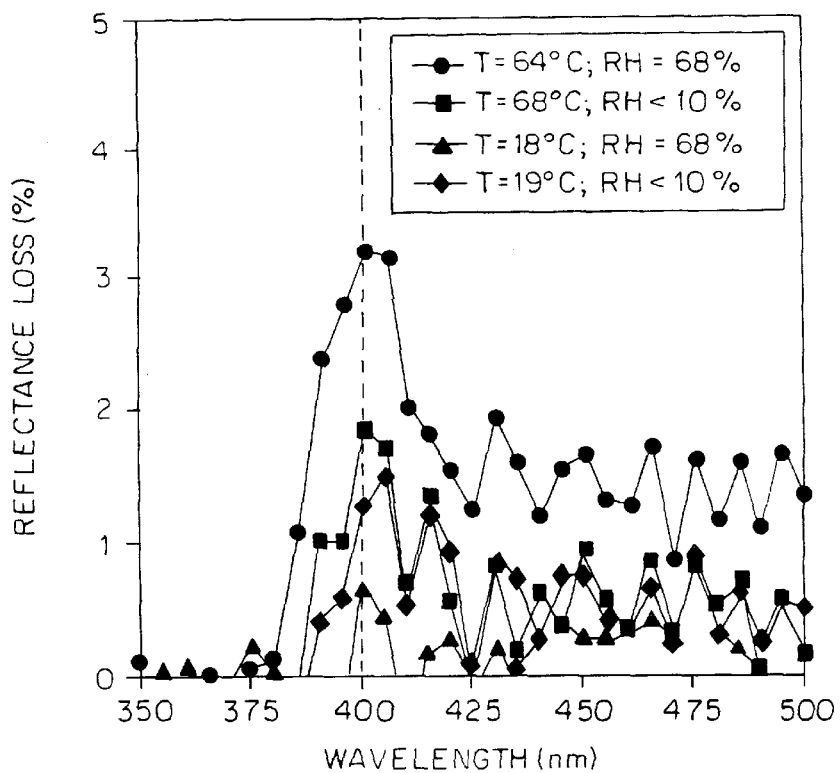
FIG. 6a is a graph showing reflectance loss for samples tested at 100×.
Figure 6B:
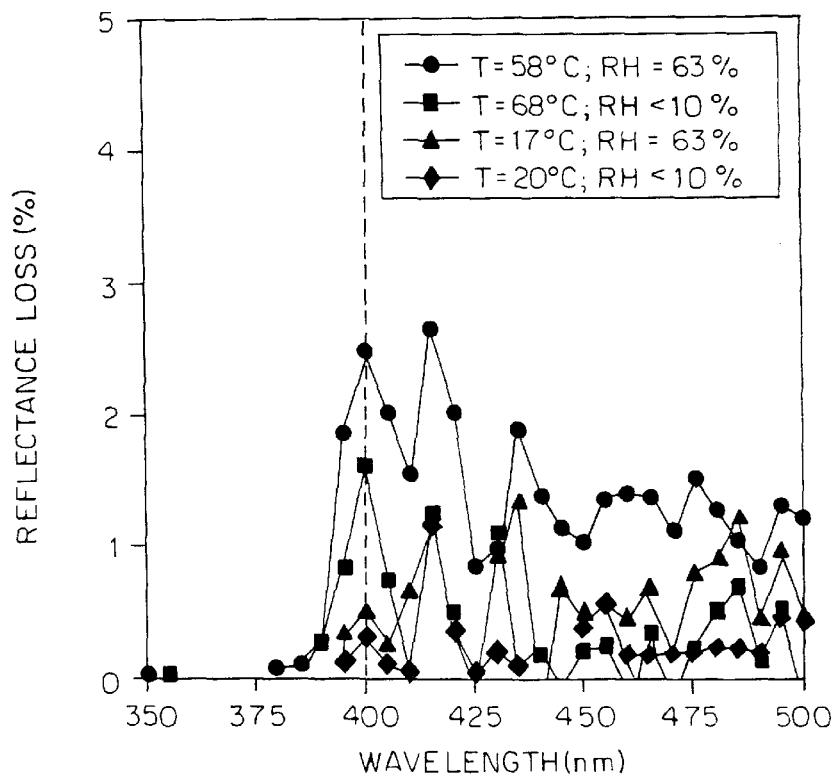
FIG. 6b is a graph showing reflectance loss for other samples tested at 75×.
Figure 6C:
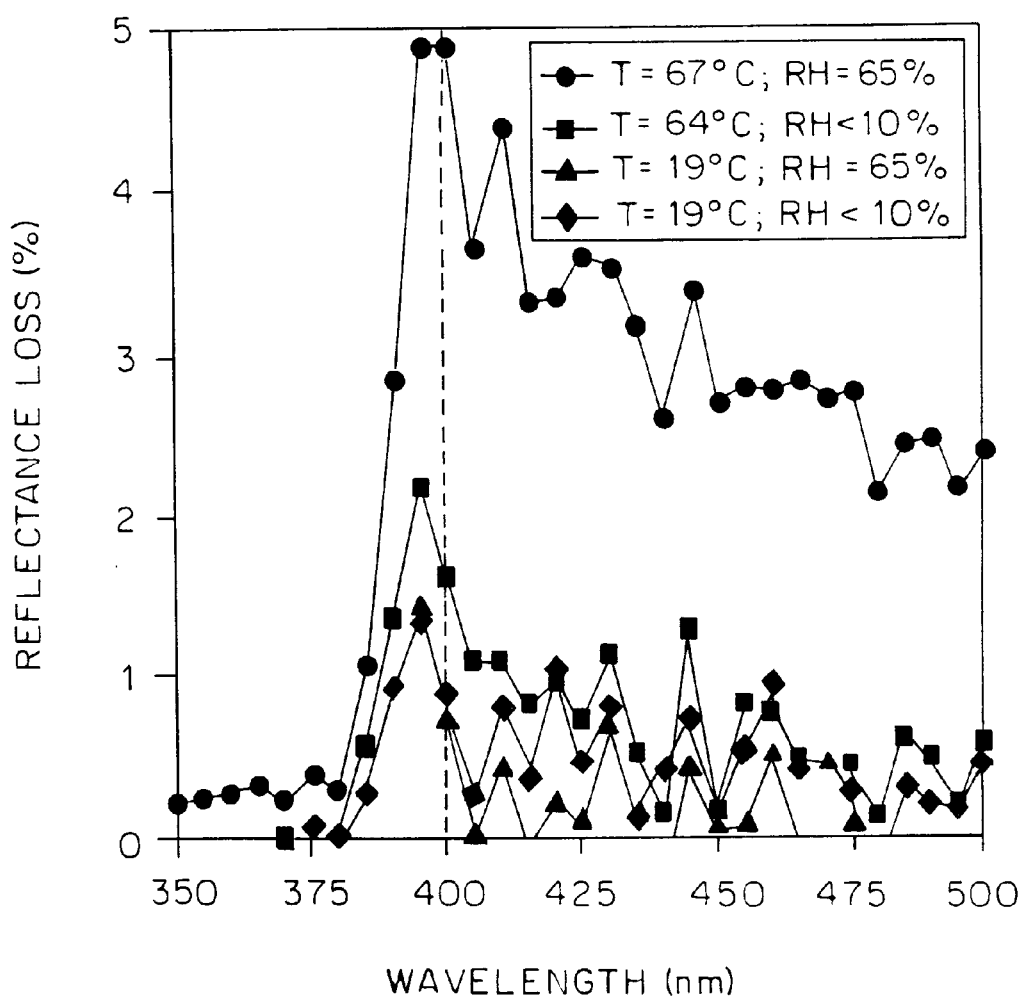
FIG. 6c is a graph showing reflectance loss for yet other samples tested at 50×.

Representative plots of spectral reflectance loss are shown in FIG. 6 for three materials and three levels of light intensity. FIG. 6a corresponds to ECP-300A material exposed at 100 suns; FIG. 6b corresponds too ECP-305 material exposed at 75 suns, and FIG. 6c corresponds to ECP-305+ material exposed at 50 suns, respectfully. Where applicable, results for replicate samples have been averaged.

Several important points can be seen in these plots. First, reflectance loss at 400 nm, $\Delta\rho_{2\pi}(400)$, (indicated by the vertical dashed grid at $\lambda$=400 nm in these graphs) is a particularly sensitive measure of degradatiton for all three materials tested. Therefore, $\Delta\rho_{2\pi}(400)$ was chosen as the best indicator of performance loss for further analysis. The effect of the various stress factors can also be seen in FIGS. 6a–c. Exposure to light at elevated temperatures is clearly the dominant stress. In general, light exposure at high temperatures and high humidity results in the greatest degradation. Exposure at high temperature but low humidity produces an intermediate loss in performance. At lower temperatures, performance loss is smallest and humidity is seen to play a less significant role. Exposure at high humidity results in only marginally increased degradation compared to low humidity when the sample temperature is kept relatively cool.

Figure 7A:
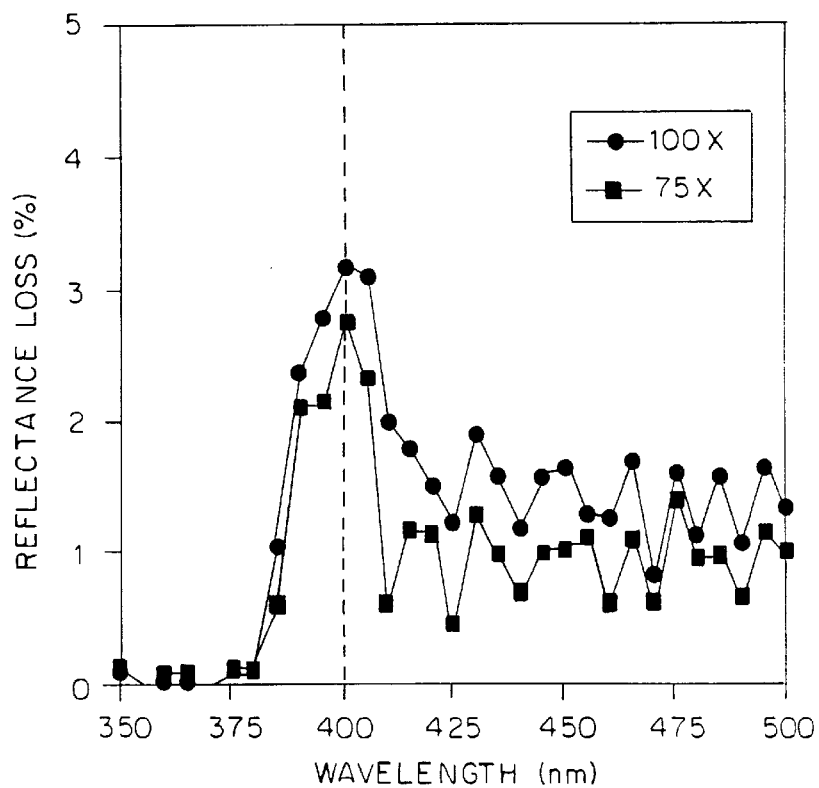
FIG. 7 shows graphs of reflectance loss for three materials as a function of light intensity exposure at T~70° C. and RH~65%.
Figure 7B:
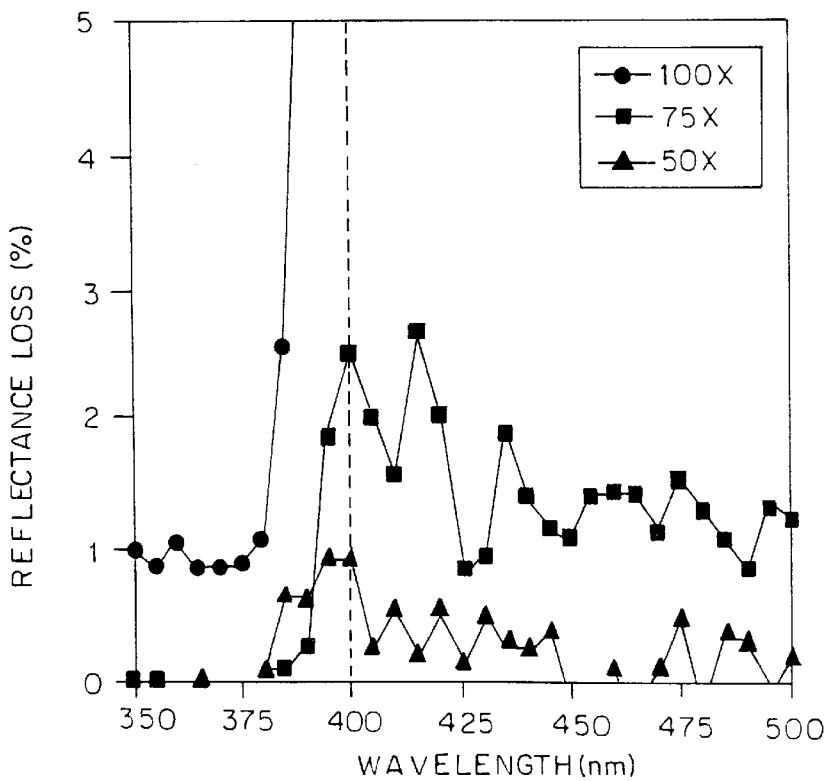
Figure 7C:
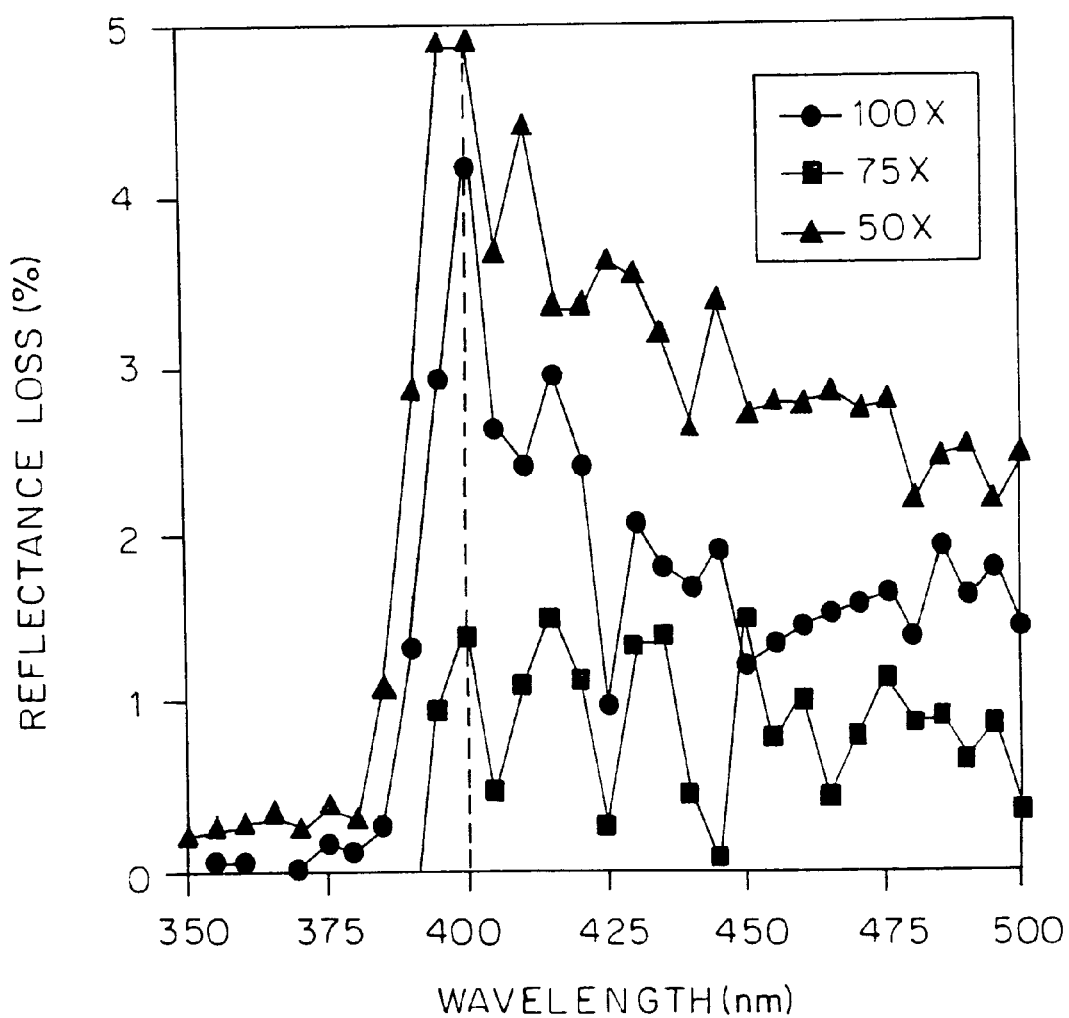

The spectral loss in reflectance (or reflectance loss) is plotted as a function of level of sunlight exposure in FIG. 7 for each material tested at the most elevated temperature and humidity conditions. FIGS. 7a–c correspond to ECP-300A, ECP-305, and ECP-305+ respectively exposed at nominally T≈70° C. and RH≈65%. As before, results for replicate samples have been averaged when applicable. The change in reflectance was calculated after a targeted cumulative dose, associated with an equivalent one year's exposure had been accumulated. The intent was to investigate two important questions. First, can these types of materials be subjectd to ultra-high levels of natural sunlight (50–100x) without introducing unrealistic failure mechanisms? Second, does a reciprocity relationship exist between the level of light intensity and time of exposure? If these questions can be answered in the affirmative, then the experimental procudures developed in this project can be used to allow reliable inferences to be made about material durability in high abbreviated time frames.

FIGS. 7a–c provide no evidence to suggest the level of light intensity results in any systematic proclivity for loss in reflectance. That is, exposure at 50 suns for some time, t, is equivalent to exposure at 100 suns for half that time, t/2. For example, in FIG. 7a, the effect os expoosure at elevated temperature and humidity at 75 suns for 32 hours is roughly the same as that resulting from exposure at 100 suns for 26.4 hours for ECP-300A. It is the cumulative dose rather than the level of intensity (within the range 50x–100x tested) that gives rise to reflectance loss. This is even more striking in FIG. 7c where the 50 sun exposure results in slightly greater degradation after 56.3 hours than either the equivalant 75 suns or 100 sun exposures for ECP-305+. The result presented in FIG. 7b are somewhat anomalous. The one sample of ECP-305 exposed at elevated temeperature and humidity at 100 suns shows considerably greater loss in performance (off scale in FIG. 7b) relative to all other materials and exposure conditions ($\Delta\rho_{2\pi}(400)$=12.7%). Visually, the polymer film superstrate of this sample appeared crazed and cloudy after exposure. This is indicative of excessive heat damage that could have been caused, for example, by short term thermal excursions during exposure. Consequently results for this sample were considered an outlier and were not used in further analyses discussed below. Other materials exposed in this quardrant of the sample chamber exhibited minor thermal damage as well. This emphasizes the importance of being able to maintain good control of sample temperature (especially at the top surface and/or in the upper stratum of layered constructions). Thus, our results not only demonstrate that ultra-high levels of natural sunlight can be reasonably used for accelerated exposure materials testing, but that we can generally prevent excessive thermal loads from causing unrealistic damage.

Returning to the type of data presented in FIGS. 7a–c, the abiliity to expose samples to the same light intensity at two (constant) levels (high and low) each of temperature and humidity allows change in performance to be related to the enviornmental stress factors. Such a relationoship is:

$$\Delta\rho = {}^*I_{UV-B} {}^* e^{-(E/T)} {}^* e^{C \cdot RH} \qquad (1)$$

where:

$I_{UV-B}$=the cumalaitive dose in the UV-B spectral range ($\lambda$=280–320 nm)

T=Temperature (K)

RH=Relative humidity (%)

and A, C, and E are parameters to be fit from the measured data, $\Delta\rho_{2\pi}(400)$.

$I_{UV-B}$ was obtianed from the spectral irradiance (scaled by the concentration factor associated with each experiment) and the length of exposure time.

Table 3 presents the values of $I_{UV-B}$ corresponding to the three experiments. Using the corresponding value of $I_{UV-B}$ and the associated values of temperature and relative humidity experienced by exposure samples, the various parameters specified in Equation (1) were computed from measured values of $\Delta\rho._{2\pi}(400)$. The resulting parameter estimates for each of the three materials tested are given in Table 4.

Figure 8:
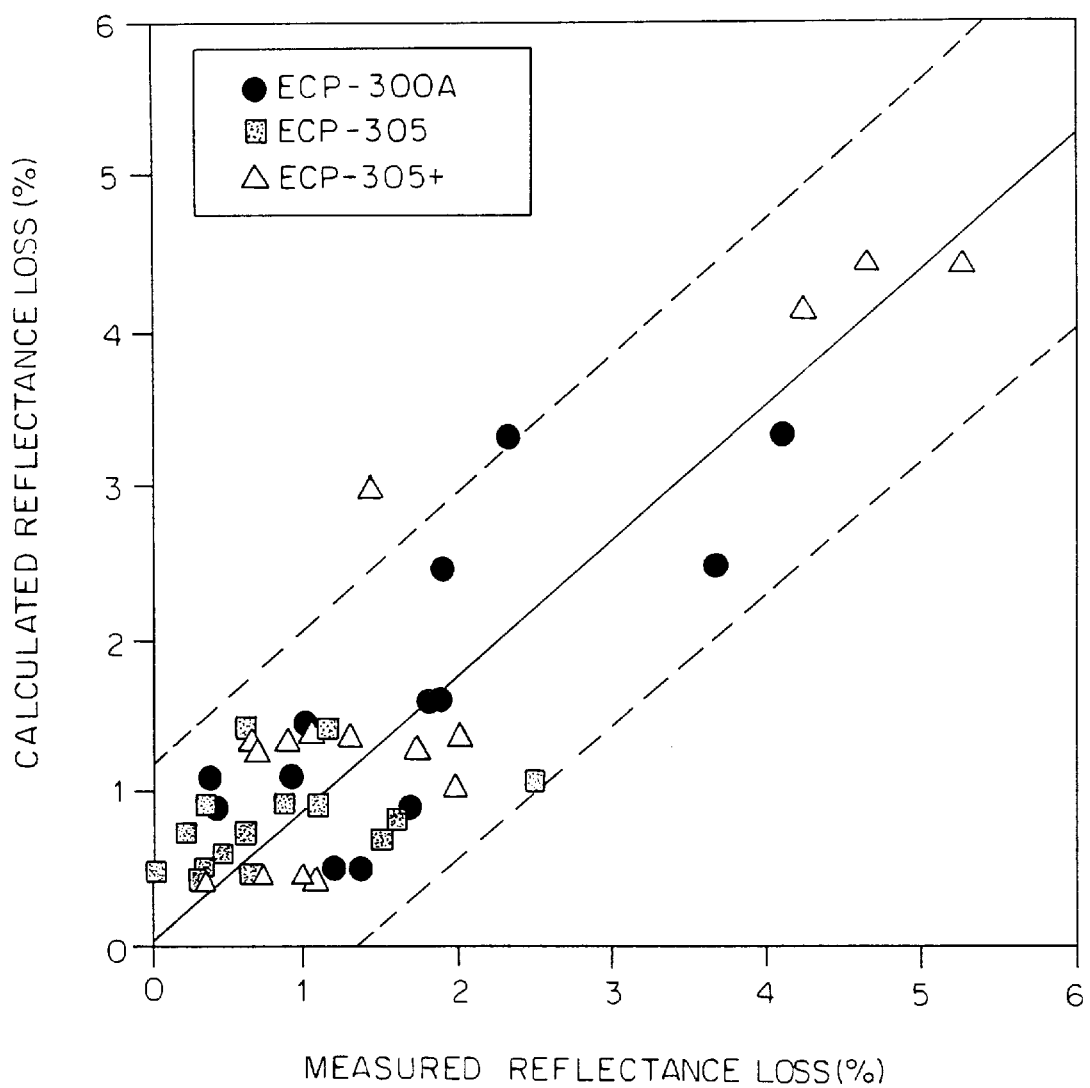
FIG. 8 shows a graph of the calculated versus measured reflectance loss.

The calculated change in performance is presented as a function of measured changes in FIG. 8. Here, data for all three materials are shown, along with a composite linear regression line (which has been constrained to intersect the origin to reflect physical reality that no degradation occurs until light exposure begins). Note that nearly all data points are contained within a 95% prediction interval associated with this regression (dashed lines). The equation for $\Delta\rho$ is seen to provide a good representation of the data. The computed slope of the regression line is 0.88 (compared to 1.0 for perfect agreement between measured and calculated values of reflectance loss).

The parameter estimated for the ECP-300A/aluminum substrate construction are in close agreement with previous results for a similar material construction (ECP-300A/paint/aluminum substrate). Of particular note is the excellent agreement in the thermal activation energy parameter, E, between the accelerated natural sunlight experiments (E=2376 K.) and the accelerated artiificial light (xeon arc) experiments (E=2339 K.). This provides further confidence in the visability of both types of highly accelerated test protocols.

TABLE 3

Cumulative UV-B Dose Experienced During Each Experiment

| Experiment # | Concentration Factor | Time of Exposure (hr) | Cumulative UV-B Dose ($MJ/m^2$) |
|---|---|---|---|
| 1 | 50 | 56.3 | 2.21 |
| 2 | 75 | 32.0 | 1.89 |
| 3 | 100 | 26.4 | 2.07 |

TABLE 4

Parameter Values for Material Constructions Tested.

| | Material | | |
|---|---|---|---|
| Parameter | ECP-300A | ECP-305 | ECP-305+ |
| A | $7.0684 \times 10^{-4}$ | $2.269 \times 10^{-5}$ | $8.4680 \pm 10^{-4}$ |
| C | 0.0139 | 0.0073 | 0.0205 |
| E | 2376 | 1376 | 2510 |

Figure 9:
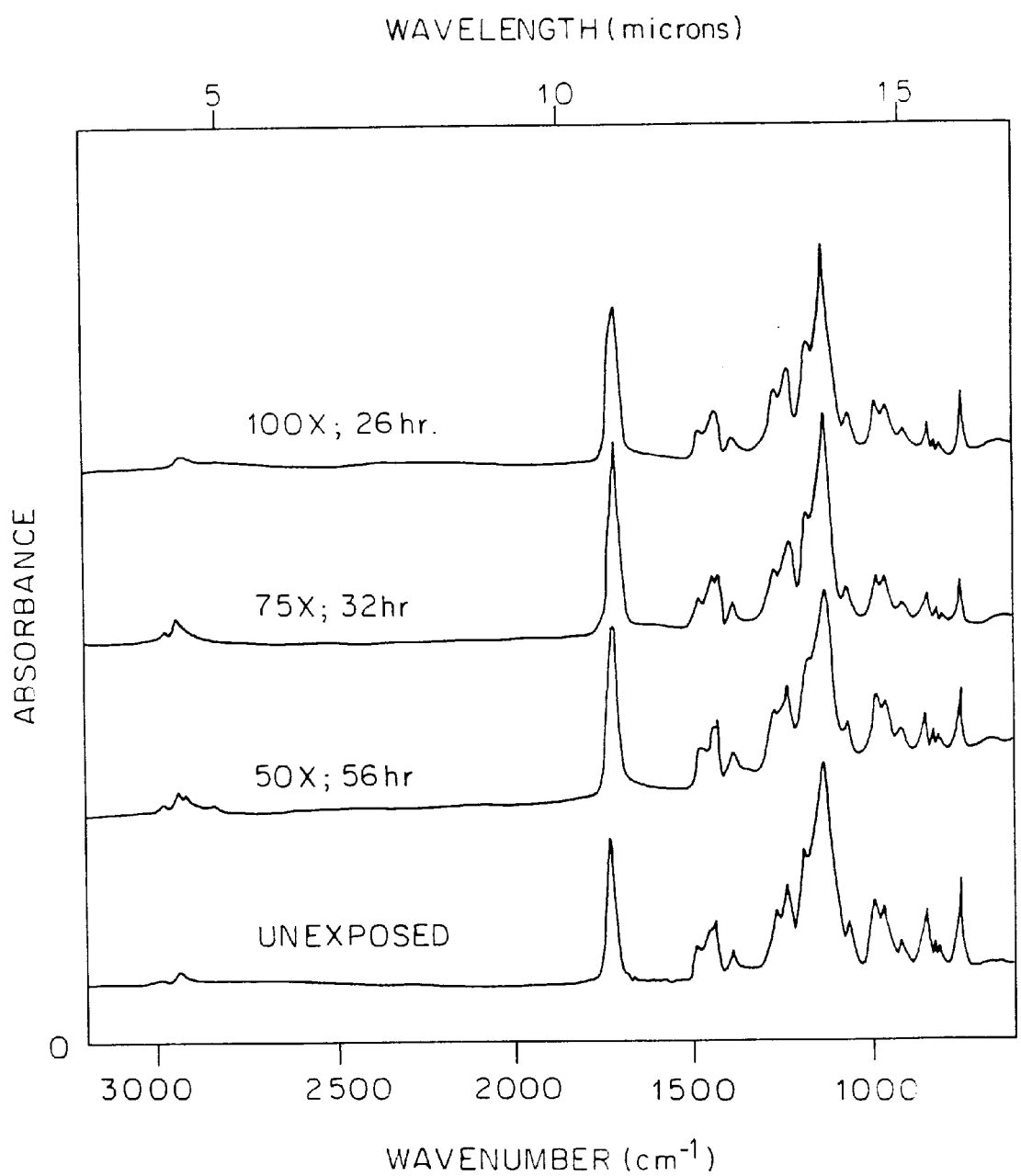
FIG. 9 shows data indicative of chemical/structural changes (or lack thereof within the bulk polymer superstrate layer of exposed mirror samples.

The results discussed above support the claim that ultra-accelerated natural sunlight exposure can be carried out, at the levels indicated and for the materials tested, without introducing unrealistic failure modes that can be quantified in terms of loss in reflectance. Although such loss is the primary performance criteria associated with these materials, other degradation may occur that would be less sensitive to this measure of performance loss. FIG. 9 presents evidence that chemical/structural changes are not being experienced within the polymer film substrate. Here, attenuated total reflectance (ATR) measurements of bulk polymer are made using Fourier transform infarred (FTIR) spectroscopy. This analytical techique is capable of detecting change in chemical bonds within materials that may be indicative of specific degradation mechanisms. FIG. 9 indicates that no substantial difference in the chemical structure occur upon exposure of 50–100x. This provides further validation of claims made below.

Conclusions

The major conclusion of these experiments was that type of solar mirror materials tested can be exposed 50–100 suns without introducing new (unrealistic) failure mechanisms. In particular, it has been demonstrated that sample temperature can be controlled sufficiently well at very high levels of solar flux without adversely effection the samples and the results.

Furthermore, a reciprocity relationship was demonstrated between time and integrated flux. That is, exposure at 50x for time t gives the same results (if all other stresses are the same) as exposure at 100x for time t/2.

Alternative Exposure Chamber Embodiment

Figure 10:
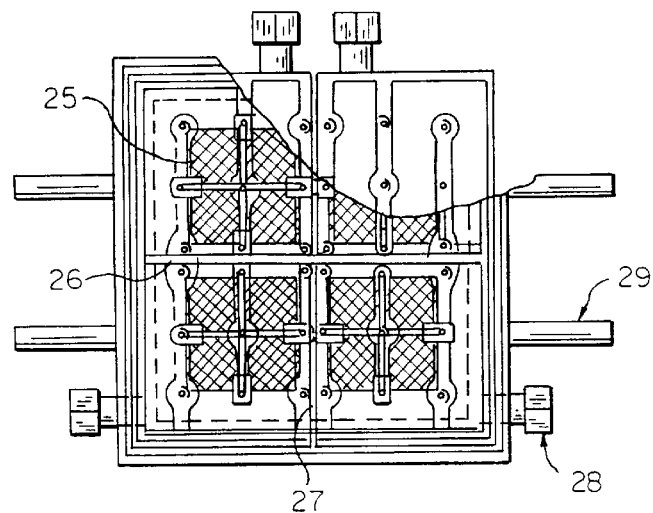
FIG. 10 shows a cut-away view of an advanced exposure chamber design in accordance with the invention.

FIG. 10 is a top view of an alternative embodiment of the exposure chamber design, showing a cut-away view. Samples 25 are disposed so that they are separated by a chamber divider 26. The chamber divider is in turn separated by an insulation divider 27. In this embodiment, larger heating/cooling ports 28 are disposed below the humidity ports 29.

Figure 11A:
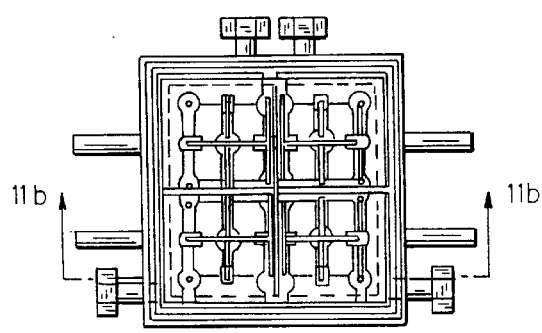
FIGS. 11a, 11b and 11c show additional views of the embodiment of the exposure chamber design of FIG. 10.
Figure 11C:
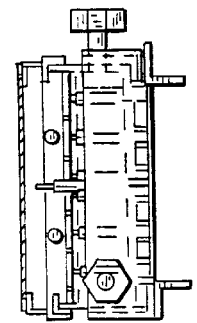

As can be seen from the embodiment in FIG. 11, a number of alternative ways exist for improving the performance and ease of use of the sample exposure chamber. For example, baffles may be added with heating and cooling using a circulating bath with an approximate range of −20 to 100° C., thereby eliminating the need for individual electric cartridge heaters that give rise to non-uniform sample exposure temperatures within a given quadrant. The baffles and chambers may be machined out of one solid block of aluminum and enlarged slightly. This would allow more room for thermocouple wires and insulation and also provide a better seal between chambers. In addition, an insulated, outside shell may be fabricated, that both chambers would rest in. This design configuration helps keep temperatures constant and makes the assembly solid.

FIG. 11a is a top view of FIG. 10 minus the samples.

Figure 11B:
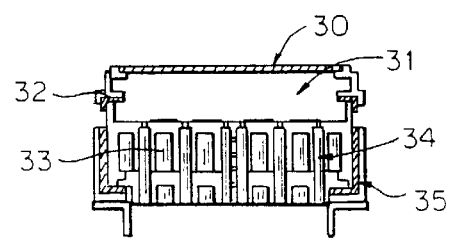

FIG. 11b is a view taken along line A—A of FIG. 11a, showing the quartz cover plate 30, the humidity chamber 31, the insulation 32, a heating/cooling chamber with baffles 33, fiber optic guides 34, and an insulated box 35, around the chambers.

The cold mirror fabricated for the invention system was comprimised of a front surface UV reflective coating (capable of reflecting between 290–350 nm and being transparent to higher wavelength light) and a second surface visible light reflector (capable of reflecting between 350–650 nm and transparent to light with $\lambda > 650$ nm).

These coatings were deposited onto either side of a 3.4 mm thick borofloat glass substrate (having a thermal coefficient of expansion of roughly $8.1 \times 10^{-6}/°$ C.). Because they are comprised of refractory oxide materials, these coatings were designed to be impervious to concentrated terrestrial sunlight. However, some absorptions of concentrated sunlight occurs within these coatings and the glass, resulting in elevated temperatures of the plate during on-sun operation.

To reduce the thermal loads of the plate, pressurized dry air (typically 60 psi) was flowed over both the front and back sides of the mirror while samples were being exposed. Cold mirror temperatures greater than 200° C. were reached at 100 suns. Concerns regarding possible shattering of the expensive cold mirror caused by thermal gradients within the plate, were further exacerbated by the possibility of thermal excursions due to transient cloud cover (in which the sun emerging from behind a cloud could momentarily deliver much higher concentration levels before the control system could react). Therefore, to provide greater cooling capacity a Vortex tube may be incorporated (a device that produces both hot and cold air from any pressurized air source) into the system design to allow cooling both sides of the mirror. Other types of cold mirrors (for example, wherein a coating applied to just one side which in operation would face the incident beam, thereby minimizing the optical path through the glass and subsequent absorbtion related thermal gradients) could be used in this design.

Alternative Embodiment Using Multi-step Parabolic Reflector

Figure 12:
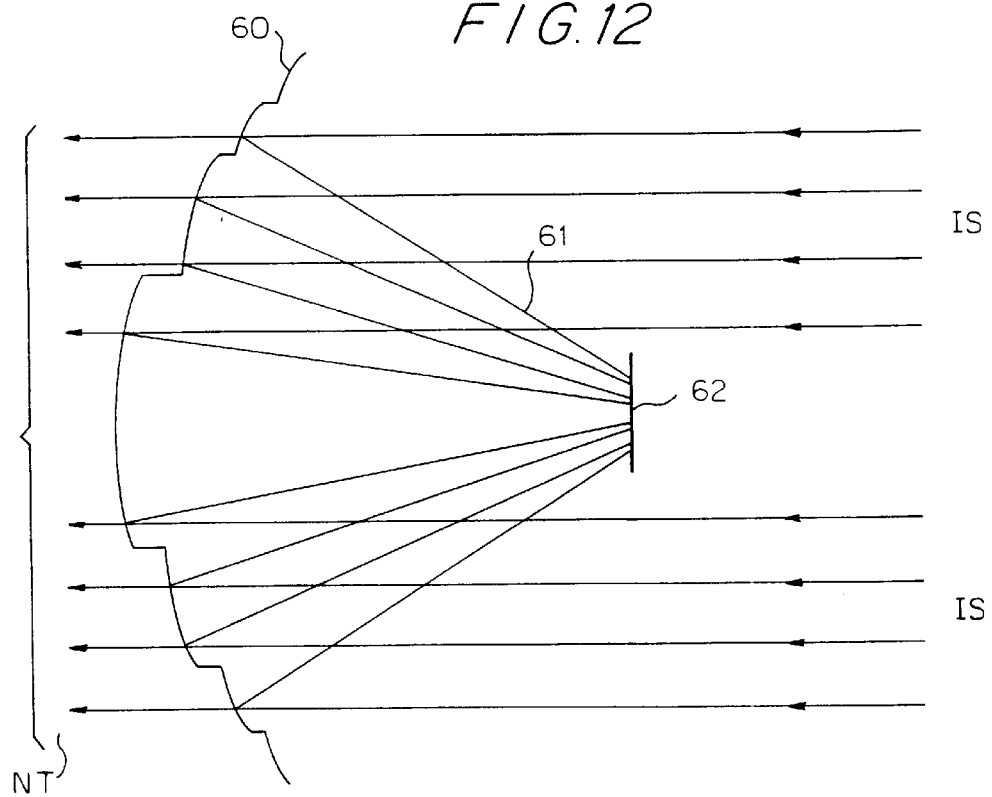
FIG. 12 shows a multi-step or multi-dish parabolic reflector used in place of a heliostat, a primary concentrator, an IRG, and a cold mirror, wherein the incident sunlight NIR segment is transmitted through the multi-dish reflector, and the UV/VIS is reflected back to the sample plane.

The invention may also be accomplished by the use of a multi-step parabolic reflector 60 as depicted in FIG. 12. The use of the multi-step dish eliminates the need for a multi-component system (heliostat, dish, IRG, cold mirror, etc.). As can be seen from FIG. 12, a multi-step parabolic dish may be utilized, and the invention may be accomplished without the use of an irradiance guide and a cold mirror as the NIR transmitted segment NT of the incident sunlight IS is transmitted through the multi-dish reflector, and the concentrated UV/VIS flux 61 is reflected back to the sample plane 62.

Figure 13:
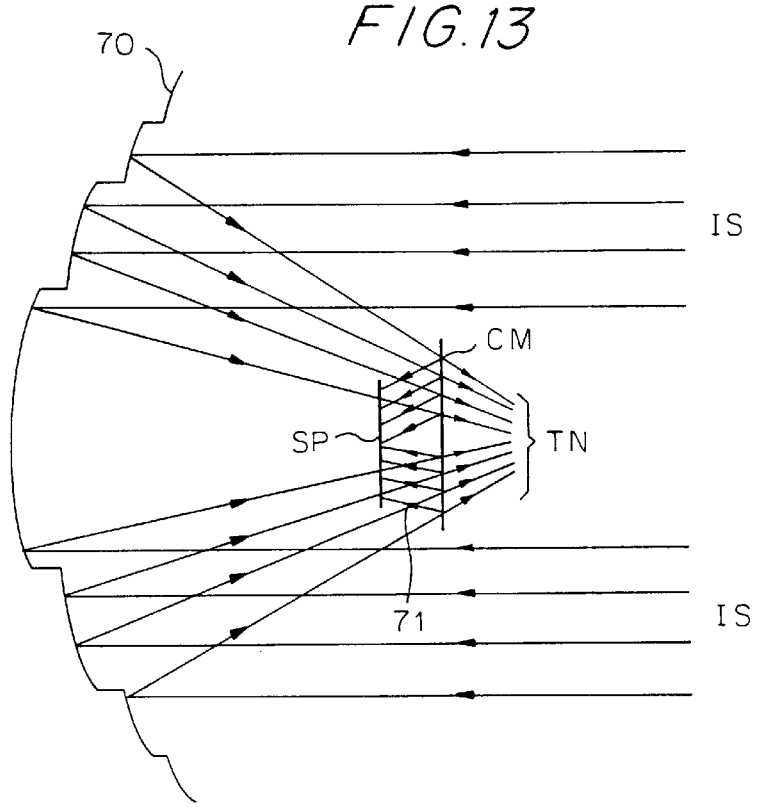
FIG. 13 shows a multi-step parabolic concentrator used in place of a heliostat, a primary concentrator, and an IRG, employing a cold mirror to reflect UV/VIS onto a sample plane.
Figure 14:
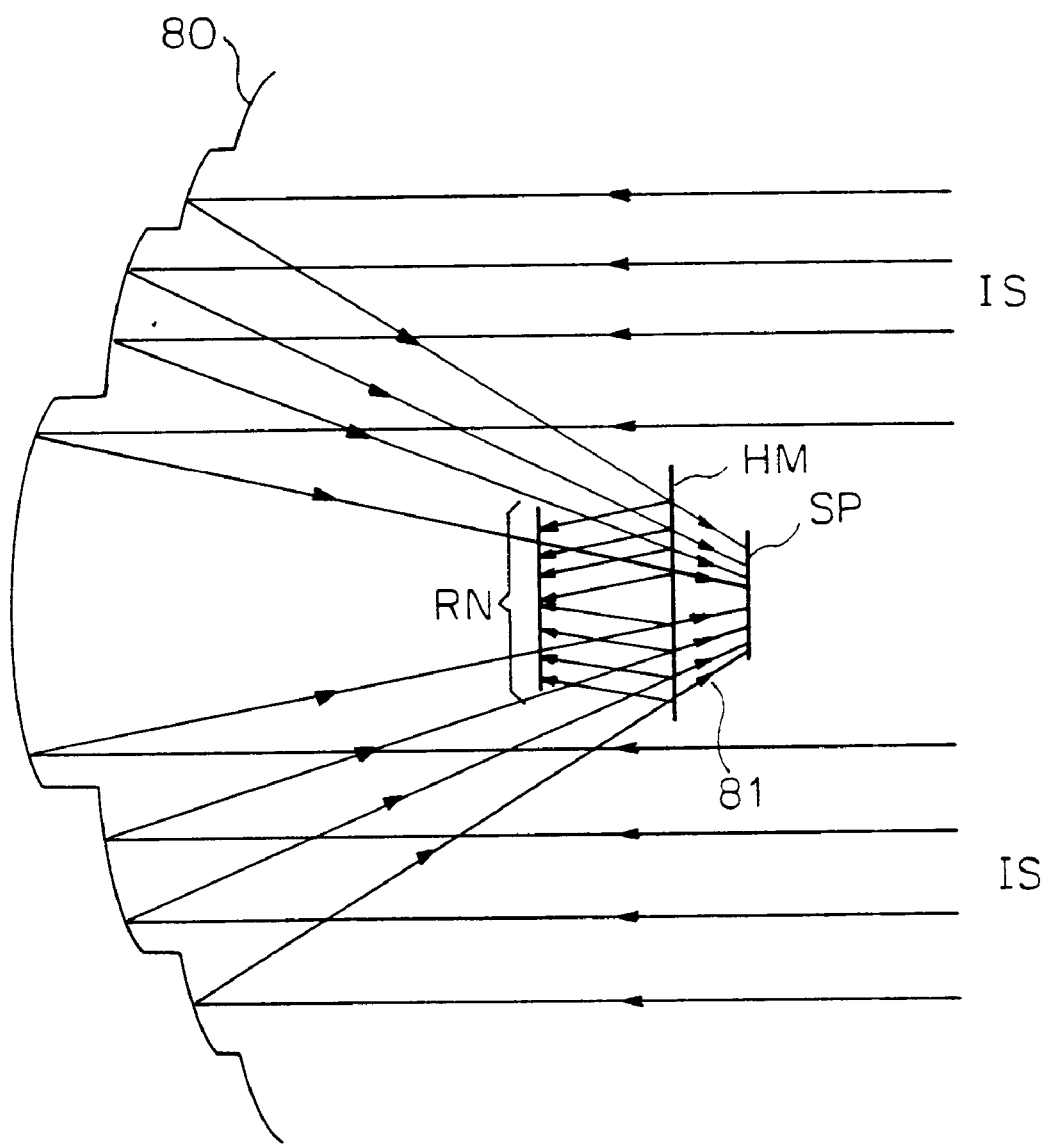
FIG. 14 shows a multi-step parabolic concentrator used in place of a heliostat, a primary concentrator, and an IRG, employing a hot mirror that transmits UV/VIS onto a sample plane and reflects NIR.

Broad band solar reflector materials can be used in conjunction with the multi-step design, thereby eliminating the need for large areas of costly spectrally selective cold mirrors located at the surface of the parabolic dish structure. One way to accomplish this using a multi-step parabolic concentrator 70, shown in FIG. 13, would be to place a smaller-area cold mirror, CM so as to intercept the concentrated sunlight and reflect the UV/VIS portion of the system, 71, back into a sample exposure chamber located at SP, while transmitting the NIR part of the spectrum, TN. Yet another way of achieving the desired result, using multi-step parabolic concentrator 80 shown in FIG. 14 would be to place a hot mirror, HM, so as to intercept the concentrated sunlight and transmit the UV/VIS portion of the spectrum, 81, into a sample exposure chamber located at SP, while reflecting the NIR part of the spectrum, RN.

We claim:

1. A process of providing ultra accelerated natural sunlight exposure testing of sample materials and devices under controlled weathering conditions that include multiple concurrent levels of temperature and relative humidity at high levels of up to 100× of natural sunlight comprising:
   a) concentrating solar flux uniformly as concentrated uniform reflected UV/VIS light; using a multi-step dish reflector; and
   b) directing said concentrated uniform reflected light onto sample materials in a chamber of multiple concurrent levels of temperature and relative humidity to allow the sample materials to be subjected to accelerated irradiance exposure factors of from about 25 to 100 suns for a sufficient period of time of about 20.1 hours to about 10 days to provide a corresponding time of about at least a years worth of representative weathering of said sample materials; wherein in step a), concentrating said solar flux uniformly is accomplished by:
      i) using a tracking heliostat to continually direct sunlight onto a primary concentrator array, to provide a concentrated sunlight Gaussian shaped beam;
      ii) passing said concentrated sunlight Gaussian-shaped beam through an attenuator to provide a reduced and controlled intensity of concentrated sunlight Gaussian-shaped beam;
      iii) passing said concentrated sunlight Gaussian-shaped beam through an irradiance redistribution guide to redistribute the Gaussian-shaped beam from the primary concentrator to a more uniform profile on a plane located a distance behind the irradiance redistribution guide; and
      iv) passing said redistributed Gaussian-shaped beam onto a cold mirror; comprising: I) a front surface UV reflective coating capable of reflecting ultraviolet light and; II) a second surface visible light reflector capable of reflecting visible light and transparent to near infrared radiation or, III) a front surface UV/VIS reflective coating capable of reflecting ultraviolet and visible light.

2. The process of claim 1 wherein the ultraviolet reflected light is from about 290 to about 350 nm and the visible reflected light is from about 350 to about 650 nm.

3. The process of claim 2 wherein said concentrated sunlight Gaussian-shaped beam is characterized by from about 25× to about 100× of concentrated natural sunlight.

4. The process of claim 3 wherein said sample materials are placed into a chamber having quadrants for testing accelerated irradiance exposure sun factors under conditions of hot and dry, hot and wet, cold and dry and cold and wet.

5. The process of claim 4 wherein exposure conditions average:

| Acceleration factor (suns) | Temperature | | Relative Humidity | |
|---|---|---|---|---|
| | Avg Hot (° C.) | Avg Cold (° C.) | Avg Wet (% RH) | Avg Dry (% RH) |
| 50 | 63–71 | 18–23 | 55–75 | 5–10 |
| 75 | 60–75 | 17–24 | 55–70 | 5–10 |
| 100 | 65–75 | 15–25 | 60–75 | 5–10 |

6. The process of claim 4 wherein said sample materials are aluminum substrates.

7. An apparatus for providing ultra accelerated natural sunlight exposure testing for sample materials and devices under controlled weathering conditions that include multiple concurrent levels of temperature and relative humidity at high levels of natural sunlight comprising: means for concentrating solar flux uniformly as concentrated uniform reflected light, and means for directing said concentrated uniform reflected light onto sample materials contained in a chamber having means to provide multiple concurrent levels of temperature and relative humidity;

wherein said means for concentrating solar flux uniformly as concentrated uniform reflected light further comprises tracking heliostat means to continually direct sunlight onto a primary concentrator array means of a high-flux solar furnace to provide a concentrated sunlight Gaussian-shaped beam; means for passing said concentrated sunlight Gaussian-shaped beam through attenuator means to provide reduced and controlled intensity of concentrated sunlight Gaussian-shaped beam; means for passing said concentrated sunlight Gaussian-shaped beam through an irradiance redistribution guide means to redistribute the Gaussian-shaped beam from primary concentrator means to a more uniform profile on a plane located a distance behind said irradiance redistribution guide means; and means to pass the redistributed Gaussian-shaped beam onto a cold mirror means combined with said chamber, said cold mirror means further comprising front surface UV reflective coating means to reflect ultraviolet light and a second surface visible light reflector means to reflect visible light and transmit near infrared radiation; and wherein said chamber is capable of receiving directed reflected light from said cold mirror means to allow the sample materials to be subjected to accelerated irradiance exposure factors for a significant period of time of about 20.1 hours to about 10 days to provide a corresponding time of about at least a years worth of the representative weathering of sample materials.

8. The apparatus of claim 7 wherein said means for concentrating solar flux uniformly as concentrated uniform reflected light is a multi-step dish reflector that transmits NIR wavelengths.

9. The apparatus of claim 7 wherein said cold mirror means provide ultraviolet reflected light from about 290–350 nm and visible reflected light from about 350 to about 650 nm.

10. The apparatus of claim 9 wherein said primary concentrator array of a high flux solar furnace means provides concentrated sunlight Gaussian shaped beam characterized by from about 25× to about 100× of concentrated natural sun light.

11. The apparatus of claim 10 wherein said chamber means have quadrants for testing accelerated irradiance exposure sun factors under conditions of hot and dry, hot and wet, cold and dry and cold and wet.

12. The apparatus of claim 11 wherein said chamber means can accomodate average exposure conditions of:

| Acceleration factor (suns) | Temperature | | Relative Humidity | |
|---|---|---|---|---|
| | Avg Hot (° C.) | Avg Cold (° C.) | Avg Wet (% RH) | Avg Dry (% RH) |
| 50 | 63–71 | 18–23 | 55–75 | 5–10 |
| 75 | 60–75 | 17–24 | 55–70 | 5–10 |
| 100 | 65–75 | 15–25 | 60–75 | 5–10. |

* * * * *